United States Patent
Boomgaarden et al.

(10) Patent No.: US 7,182,511 B2
(45) Date of Patent: Feb. 27, 2007

(54) CEILING MOUNTED X-RAY TUBE SUPPORT

(75) Inventors: Jonathan Carl Boomgaarden, Waukehsa, WI (US); Michael John Pajerski, Oconomowoc, WI (US)

(73) Assignee: General Electric Company, Schnectady, NY (US)

(*) Notice: Subject to any disclaimer, the term of this patent is extended or adjusted under 35 U.S.C. 154(b) by 0 days.

(21) Appl. No.: 10/904,737

(22) Filed: Nov. 24, 2004

(65) Prior Publication Data

US 2006/0109955 A1    May 25, 2006

(51) Int. Cl.
*H05G 1/02*    (2006.01)
(52) U.S. Cl. .................................................. 378/197
(58) Field of Classification Search ......... 378/193–197
See application file for complete search history.

(56) References Cited

U.S. PATENT DOCUMENTS

| | | | | |
|---|---|---|---|---|
| 3,281,598 A | * | 10/1966 | Hollstein | 378/179 |
| 3,360,647 A | * | 12/1967 | Avery | 378/68 |
| 4,412,346 A | * | 10/1983 | Takenouti et al. | 378/181 |
| 4,816,617 A | * | 3/1989 | Valosen | 174/86 |
| 5,048,070 A | * | 9/1991 | Maehama et al. | 378/197 |
| 5,636,259 A | * | 6/1997 | Khutoryansky et al. | 378/197 |
| 6,155,713 A | * | 12/2000 | Watanabe | 378/197 |
| 6,926,442 B2 | * | 8/2005 | Stockl | 378/197 |

* cited by examiner

*Primary Examiner*—Courtney Thomas
(74) *Attorney, Agent, or Firm*—Peter J. Vogel

(57) ABSTRACT

A ceiling mount x-ray imaging assembly is provided comprising a track assembly. A carriage assembly is mounted to the track assembly and allows linear movement of said carriage assembly. An extendable column is rotatably mounted to the carriage assembly and has a carriage mount end and a patient directional end. The carriage mount end is rotatable about a vertical axis located at a vertical rotation location positioned in proximity to the carriage mount end. An x-ray tube assembly is rotatably mounted to the extendable column adjacent a patient directional end and is rotatable about a horizontal axis located at a horizontal rotation location positioned. A communication cable assembly provides communication between the x-ray tube assembly and the carriage assembly. The vertical rotation location and the horizontal rotation location are positioned at opposing ends of the extendable column.

20 Claims, 1 Drawing Sheet

CEILING MOUNTED X-RAY TUBE SUPPORT

TECHNICAL FIELD

The present invention relates generally to an x-ray tube support and more particularly to an x-ray tube support with improved mechanical structure.

BACKGROUND OF THE INVENTION

Medical imaging continues to expand into a wide range of patient diagnostic procedures. In doing so, imaging equipment must be suitable to provide an increasing range of images for an increasing range of body regions. The nature, however, of x-ray imaging dictates that the x-ray stream must be directionally controlled through the patient such that specific body images are developed. As such, it is common for the x-ray generating element of a medical imaging assembly to be movable through a plurality of positions relative to the patient to allow for proper orientation.

Another quality of x-ray imaging equipment is that is it commonly bulky and weight intensive. Increased size and weight characteristics make positioning of the x-ray generating element difficult. Often, existing positioning mechanics result in oversized, difficult to manage assemblies. This is clearly not desirable. In one known arrangement, the medical imaging assembly is mounted to the ceiling within a room. The emitting element is mounted to a telescoping support mounted to the ceiling. The emitting element can, thereby, be lowered in relation to the patient. The emitting element is commonly mounted to the bottom of the telescoping element such that it can be aimed in a particular direction and plane.

This arrangement, however, generates structural concerns. Rotation around multiple axes at the bottom of a telescoping mount can result in increased structure at the bottom of the mount. This, in turn, can require a more massive and structurally sound mount. As the mount increasing in structure, it becomes more difficult for the tube mount emitter to be able to clear the column in all positions. This can result in the tube mount to be attached to the extreme bottom of the column and to be offset to clear the column. Again, the size of the structure is undesirably increased. In addition, the routing of cables required for operation of the tube and collimator must be arranged and routed so as to compensate for the tube being rotated about a dual axis in a single location. This may limit the range of rotation of the tube mount, or may limit the placement of the cables.

It would, therefore, be highly desirable to have a medical imaging assembly with improved x-ray tube mounting. Additionally, it would be highly desirable to have an x-ray tube mount assembly that reduced the weight at the bottom of the telescoping mount, reduced rotational interference of the x-ray tube mount with the telescoping mount, and provided improvements to the routing of cables to support the x-ray tube mount.

SUMMARY OF THE INVENTION

A ceiling mount x-ray imaging assembly is provided comprising a track assembly. A carriage assembly is mounted to the track assembly and allows linear movement of said carriage assembly. An extendable column is rotatably mounted to the carriage assembly and has a carriage mount end and a patient directional end. The carriage mount end is rotatable about a vertical axis located at a vertical rotation location positioned in proximity to the carriage mount end. An x-ray tube assembly is rotatably mounted to the extendable column adjacent a patient directional end and is rotatable about a horizontal axis located at a horizontal rotation location positioned. A communication cable assembly provides communication between the x-ray tube assembly and the carriage assembly. The vertical rotation location and the horizontal rotation location are positioned at opposing ends of the extendable column.

Other features of the present invention will become apparent when viewed in light of the detailed description of the preferred embodiment when taken in conjunction with the attached drawings and appended claims.

DESCRIPTION OF THE PREFERRED EMBODIMENTS

Figure 1:
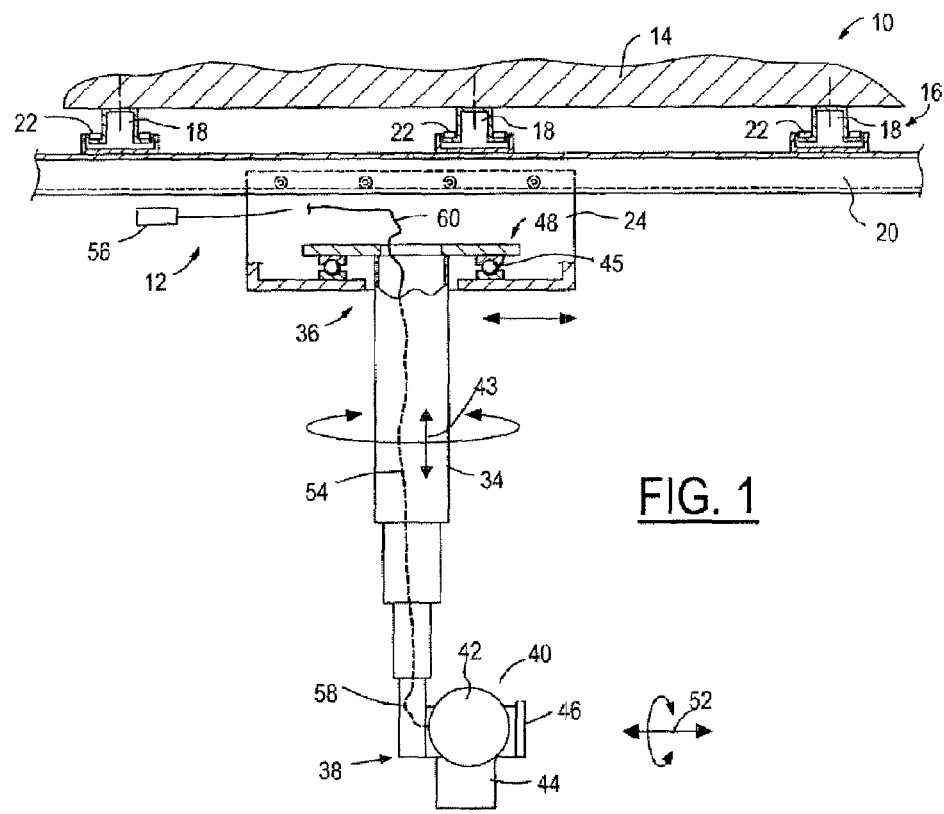
FIG. 1 is a side view illustration of a medical imaging assembly in accordance with the present invention.
Figure 2:
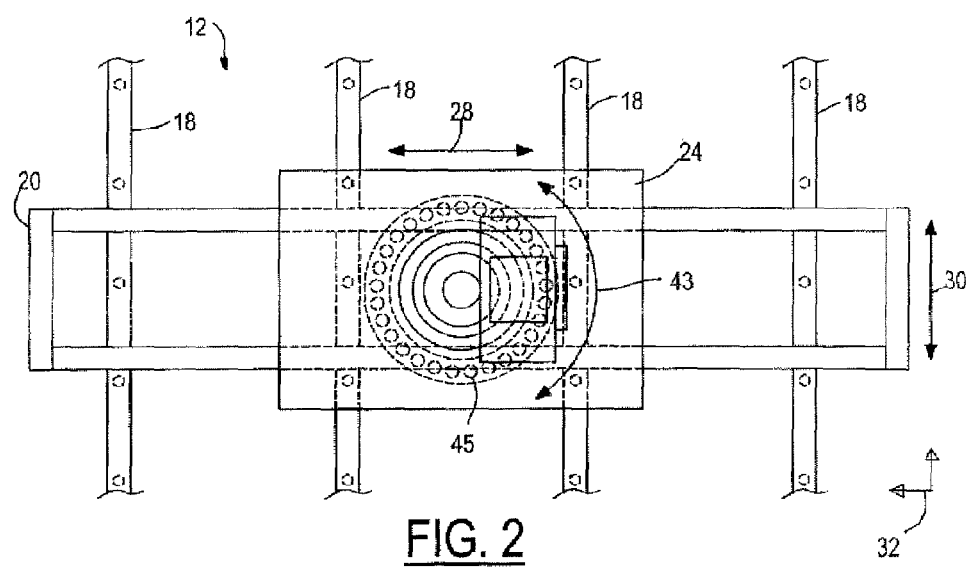
FIG. 2 is a top view illustration of the medical imaging assembly illustrated in FIG. 1.

Referring now to FIGS. 1 and 2 which are illustrations of an imaging assembly 10 in accordance with the present invention. The imaging assembly 10 includes a ceiling mount imaging assembly 12 mounted to a ceiling 14 or similar surface. The ceiling mount imaging assembly 12 of the present invention provides a novel and unique arrangement that provides improved operation and novel adjustment features.

The present invention accomplishes these novel mechanical adjustments through the use of a track assembly 16 mounted to the ceiling 14 or similar first surface. Although a variety of track assemblies 16 are contemplated, one embodiment includes a primary stationary rail assembly 18 mounted to the ceiling 14. A secondary rail assembly 20 is slidably engaged to said primary stationary rail assembly 18 such that it is movable to a plurality of positions along said primary rail assembly 18. Although the connection may be accomplished in a variety of mechanical fashions, a rail roller bearing assembly 22 mounted to the secondary rail assembly 20 and rotatably engaging the primary rail assembly 18 is contemplated. The secondary rail assembly 20 is preferably orientated perpendicular to said primary rail assembly 18. In this fashion the track assembly 16 provides a range of positions along a primary plane coincident with the ceiling 14. A carriage assembly 24 is slidably engaged to said secondary rail assembly 20 by way of a carriage transfer bearing assembly 26. Thus the carriage assembly 24 is movable in a first transfer direction 28 and a secondary direction 30 to be positionable throughout the primary track plane 32 (see FIG. 2).

It is desirable for the generation of x-rays to be positioned relatively close to the desired target. As such, the present invention includes an extendable column assembly 34 such as a telescoping column. The extendable columns assembly 34 includes a carriage mount end 36 and a patient directional end 38. The patient directional end 38 is movable towards and away from the carriage mount end 36 such that the patient directional end 38 may be positioned close to the imaging surface. An x-ray tube assembly 40 is mounted to the extendable column assembly 34 in proximity to the patient directional end 38 such that x-ray generation may be provided in close proximity to any imaging surface. The x-ray tube assembly 40 preferably includes an x-ray tube element 42, a collimeter 44, and a user interface 46.

In addition to vertical positioning of the x-ray tube assembly 40 using the extendable column assembly 34 and transitional positioning using the track assembly 16, it is desirable to angle the x-ray tube element 42 and collimeter 44 to aim the x-ray tube element 42 precisely at a desired imaging surface. The present invention utilizes a unique method of providing this positioning while limiting the weight and bulk at the patient directional end 38 of the column 34. This reduces stress within the column 34, eases motion along the track assembly 16, and reduces incidents of interference with the column 34 by the x-ray tube assembly 40. This is accomplished by providing a first rotational axis 43 (vertical) at the carriage mount end 36 of the column assembly 34. A circular bearing assembly 45 mounted at this vertical rotation location 48 allows the entire column 34 to rotate about the first rotational axis 43 (vertical rotational axis). By moving the vertical rotation to the carriage mount end 36, the patient directional end 38 is reduced in weight and additional structure is removed.

In addition, moving the vertical rotation location 48 to the carriage mount end 36, the structure at the patient directional end 38 may be reduced to provide rotational motion about only the horizontal rotational axis 52 (secondary rotational axis) through the use of a second rotational axis 52. This allows the x-ray tube assembly 40 to be mounted to the side surface 54 of the column assembly 34 which in turn allows free rotation about the second rotational axis 52 without interference with the column 34 itself. Additionally, the user interface 46 remains perpendicular to the horizontal axis 52. This allows an improved interface which remains more easily accessible to operators. The weight at the patient directional end 38 is reduced by the weight of the circular bearing assembly 44 and thereby allows easier movement and reduced structure to hold the x-ray tube assembly 40 in place.

The present invention includes a communication cable assembly 54 that places the x-ray tube assembly 40 in communication with remote control structure such as a control processor 56. The present invention allows for reduced interference in routing of the communication cable assembly 54 by allowing the cable assembly 54 to have a first cable transition portion 58 remote from a second cable transition portion 60. The first cable transition portion 58 is positioned adjacent the patient directional end 38 and is only rotated about the horizontal rotational axis 52. This provides simple routing structure that reduces stress on the cable assembly 54 and prevents interference with the column 34 during rotation of the x-ray tube assembly 40. The second cable transition portion 60 is only rotated about the vertical rotational axis 42. This additionally allows for improved routing as the cable assembly 54 has only a single rotational transition at the carriage mount end 36. The improved routing nature of this cable assembly 54 allows it to be positioned within the column 34 as previously difficult due to previous transitions required to rotate about multiple axis.

While particular embodiments of the invention have been shown and described, numerous variations and alternative embodiments will occur to those skilled in the art. Accordingly, it is intended that the invention be limited only in terms of the appended claims.

What is claimed is:

1. A ceiling mount x-ray imaging assembly comprising:
  a track assembly;
  a carriage assembly mounted to said track assembly, said track assembly allowing linear movement of said carriage assembly;
  an extendable column rotatably mounted to said carriage assembly, said extendable column having a carriage mount end and a patient directional end, said carriage mount end rotatable about a vertical axis located at a vertical rotation location positioned in proximity to said carriage mount end;
  an x-ray tube assembly rotatably mounted in direct proximity to said extendable column adjacent said patient directional end, said x-ray tube assembly rotatable about a horizontal axis located at a horizontal rotation location positioned in proximity to said patient directional end; and
  a communication cable assembly providing communication between said x-ray tube assembly and said carriage assembly;
  wherein said vertical rotation location and said horizontal rotation location are positioned at opposing ends of said extendable column.

2. A ceiling mount x-ray imaging assembly as described in claim 1, wherein said track assembly comprises:
  a primary stationary rail assembly; and
  a secondary rail assembly perpendicular to said primary stationary rail assembly, said secondary rail assembly slidably engaged to said primary stationary rail assembly, said carriage assembly slidably engaged to said secondary rail assembly.

3. A ceiling mount x-ray imaging assembly as described in claim 1, further comprising:
  a circular bearing assembly positioned between said carriage mount end and said carriage assembly such that said extendable column is rotatable about a vertical axis relative to said carriage assembly.

4. A ceiling mount x-ray imaging assembly as described in claim 1, wherein said extendable column comprises a telescopic column.

5. A ceiling mount x-ray imaging assembly as described in claim 1, wherein said x-ray tube assembly is mounted to an extendable column side surface in proximity to said patient directional end.

6. A ceiling mount x-ray imaging assembly as described in claim 1, wherein said tube assembly comprises:
  an x-ray tube element;
  a user interface mounted to said x-ray tube element, said user interface orientated perpendicular to said horizontal rotational axis; and
  a collimator mounted to said x-ray tube element.

7. A ceiling mount x-ray imaging assembly as described in claim 1, wherein said communication cable comprises:
  a first cable transition portion positioned in proximity to said patient directional end, said first cable transition portion rotated only about said horizontal rotational axis; and
  a second cable transition portion positioned in proximity to said carriage mount end, said second cable transition portion rotated only about said vertical rotational axis.

8. A ceiling mount x-ray imaging assembly as described in claim 1, further comprising:
  a first rotation element providing rotation of said x-ray tube assembly about said vertical axis; and
  a second rotational element providing rotation of said x-ray tube assembly about said horizontal axis;
  wherein said first rotation element is positioned on said carriage mount end to reduce weight at said patient directional end.

9. An x-ray Imaging assembly comprising:
a carriage assembly movable between a plurality of positions;
an extendable column rotatably mounted to said carriage assembly, said extendable column having a carriage mount end and a patient directional end, said carriage mount end rotatable about a first axis located at a first rotation location positioned in proximity to said carriage mount end; and
an x-ray tube assembly rotatably mounted to said extendable column adjacent said patient directional end, said x-ray tube assembly rotatable about a second axis located at a second rotation location positioned in proximity to said patient directional end;
wherein said first rotation location and said second rotation location are positioned at opposing ends of said extendable column.

10. An x-ray imaging assembly as described in claim 9, further comprising:
a communication cable assembly providing communication between said x-ray tube assembly and said carriage assembly.

11. An x-ray imaging assembly as described in claim 9, further comprising:
a primary stationary rail assembly; and
a secondary rail assembly perpendicular to said primary stationary rail assembly, said secondary rail assembly slidably engaged to said primary stationary rail assembly, said carriage assembly slidably engaged to said secondary rail assembly.

12. An x-ray imaging assembly as described in claim 9, wherein further comprising;
a first rotation element providing rotation of said x-ray tube assembly about said first rotational axis; and
a second rotational element providing rotation of said x-ray tube assembly about said second rotational axis;
wherein said first rotation element is positioned on said carriage mount end to reduce weight at said patient directional end.

13. An x-ray imaging assembly as described in claim 9, further comprising:
a circular bearing assembly positioned between said carriage mount end and said carriage assembly such that said extendable column is rotatable about a vertical axis relative to said carriage assembly.

14. An x-ray imaging assembly as described in claim 9, wherein said extendable column comprises a telescopic column.

15. An x-ray imaging assembly as described in claim 9, wherein said x-ray tube assembly is mounted to an extendable column side surface in proximity to said patient directional end.

16. An x-ray imaging assembly as described in claim 10, wherein said communication cable comprises:
a first cable transition portion positioned in proximity to said patient directional end, said first cable transition portion rotated only about said second rotational axis; and
a second cable transition portion positioned in proximity to said carriage mount end, said second cable transition portion rotated only about said first rotational axis.

17. A method of improving positioning of an x-ray tube assembly within an x-ray imaging assembly comprising:
mounting a carriage assembly on a track assembly such that said carriage assembly is movable throughout a plurality of positions;
mounting an extendable column to said carriage assembly by way of a first rotational element positioned between a carriage mount end of said extendable column and said carriage assembly, said first rotational element allowing said extendable column to rotate about a vertical rotational axis;
mounting an x-ray tube assembly in direct proximity to said extendable column by way of a second rotational element positioned at a patient directional end, said second rotational element allowing said x-ray tube assembly to rotate about a horizontal rotational axis, said first rotational element positioned remotely from said second rotational element such that said patient directional end is reduced in weight.

18. A method of improving positioning of an x-ray tube assembly within an x-ray imaging assembly comprising as described in claim 17, further comprising;
mounting said x-ray tube assembly on an extendable column side surface in proximity to said patient directional end such that said x-ray tube assembly can rotate about said horizontal rotational axis without interference from said extendable column.

19. A method of improving positioning of an x-ray tube assembly within an x-ray imaging assembly comprising as described in claim 17, further comprising:
routing a communication cable assembly from said x-ray tube assembly to said carriage assembly such that said communication cable assembly forms a first cable transition portion in proximity to said patient directional end and a second cable transition portion in proximity to said carriage mount end, said first cable transition portion rotating solely about said horizontal rotational axis, said second cable transition portion rotating solely about said vertical rotational axis.

20. A method of improving positioning of an x-ray tube assembly within an x-ray imaging assembly comprising as described in claim 17, further comprising:
mounting all positional adjustment elements with the exception of said second rotational element to said carriage mount end of said extendable column such that weight at said patient directional end is minimized.

* * * * *